United States Patent [19]
Van Wie et al.

[11] Patent Number: 5,736,342
[45] Date of Patent: Apr. 7, 1998

[54] BIOSENSOR FOR DETECTING THE PRESENCE OF CHOSEN ANALYTES

[75] Inventors: Bernard J. Van Wie; William C. Davis; David F. Moffett; Alan R. Koch, all of Pullman, Wash.; Moris Silber, Moscow, Id.; Steven R. Reiken, Medford, Mass.; Himawan Sutisna, Bandung, Indonesia

[73] Assignee: Washington State University Research Foundation, Pullman, Wash.

[21] Appl. No.: 555,347

[22] Filed: Nov. 8, 1995

Related U.S. Application Data

[63] Continuation of Ser. No. 124,914, Sep. 21, 1993, abandoned.
[51] Int. Cl.$^6$ .................................................. G01N 33/53
[52] U.S. Cl. ...................... 435/7.2; 435/7.8; 435/501; 435/512; 435/518; 435/819
[58] Field of Search .................................. 204/403–418; 356/318; 435/7.21, 7.9–7.95, 817, 7.2, 7.8; 436/518, 528, 532, 533, 806, 501, 512, 519

[56] References Cited

U.S. PATENT DOCUMENTS

| | | |
|---|---|---|
| H201 | 1/1987 | Yager . |
| 4,444,878 | 4/1984 | Paulus et al. . |
| 4,474,893 | 10/1984 | Reading . |
| 4,508,831 | 4/1985 | Toth . |
| 4,661,235 | 4/1987 | Krull et al. . |
| 4,849,509 | 7/1989 | Thurin et al. . |
| 4,874,499 | 10/1989 | Smith et al. . |
| 5,001,048 | 3/1991 | Taylor et al. . |
| 5,045,535 | 9/1991 | Mang . |
| 5,111,221 | 5/1992 | Fare et al. . |
| 5,192,507 | 3/1993 | Taylor et al. . |
| 5,204,239 | 4/1993 | Gittep et al. . |
| 5,234,566 | 8/1993 | Osman et al. . |
| 5,239,059 | 8/1993 | Zaslott et al. . |
| 5,328,847 | 7/1994 | Case et al. . |
| 5,368,712 | 11/1994 | Tomich et al. . |
| 5,436,170 | 7/1995 | Cornell et al. . |

OTHER PUBLICATIONS

Blatt, Y. et al. "Monoclonal Antibodies Specific to the β and γ subunits of the Torpedo Acetylcholine Receptor Inhibit Single–Channel–Activity". J. Neuroscience 6(2)481–5, 1986.
Kiefer, H. et al. "Biosensors based on membrane transport proteins". Biosensors & Bioelectronics 6 (1991) 233–237.
Herbert, W.J. et al. Dictionary of Immunology Boston: Blackwell Scientific Publications, 1985, p. 55.
Science, vol. 229 (Jul. 5, 1985) pp. 81–83.
Analytical Letters, 20(6), 857–870 (1987).
Analytica Chimica Acta 213 (1988) 131–138.
Analytical Letters, 21(9), 1665–1680 (1988).
Biosensor Technology–Fundamentals and Applications (Marcel Dekker, Inc.) 1990, Chapters 9 and 29.
Analytical Sciences, Apr. 1990, vol. 6, 221–225.
Bioprocess Technology 14, 263–303 (1991).

*Primary Examiner*—Marianne P. Allen
*Assistant Examiner*—Patricia A. Duffy
*Attorney, Agent, or Firm*—Richard F. Fennelly; Louis A. Morris

[57] ABSTRACT

The present invention relates to a biosensor for detecting the presence of an analyte in solution. The biosensor is composed of:
a) an ion channel receptor immobilized in a suspended lipid film which is in contact with an ion-containing solution on each side thereof;
b) a ligand, conjugated to the receptor, which has particular affinity for the analyte in solution, and, which, upon binding to the analyte in solution, causes an inhibition in ion flow through the channel; and
c) means to detect the inhibition of ion flow through the channel in response to the binding of conjugated ligand and analyte.

18 Claims, 7 Drawing Sheets

FAB' + ANTI (FAB') 2  50 μl PF  VESICLES
VERTICAL GAIN = 2X

FAB' 50 μl OF VESICLES
VERTICAL GAIN = 2X $dF/F = .10$

CONTROL 100 μl OF VESICLES

SLOW TIME (TICS 50/10 SEC/IN)

$dF/F = .22$

ANTIBODY ACTIVITY VIA ELISA

|  | EXPERIMENTAL | | | | CONTROLS | |
|---|---|---|---|---|---|---|
|  | mAb<br>1:1000 | bAb<br>1:1000 | bAb<br>w/Bov IgG<br>1:1000 | Dilution<br>ABS | Big 715<br>1:1000 | MAb148<br>w/Bov IgG<br>1:1000 |
| anti-Rat<br>(fAB') | 2.25 | 1.85 | 1.75 |  | 0.04 | 0.05 |
| anti-Mouse<br>(fAB') | 1:1000<br>0.05 | 1:1000<br>1.72 | 1:1000<br>1.80 | Dilution<br>ABS | 1:1000<br>0.03 | 1:1000<br>0.02 |
| anti-Bov IgG | 1:1000<br>0.04 | 1:1000<br>0.06 | 1:1000<br>1.63 | Dilution<br>ABS | 1:1000<br>0.02 | 1:1000<br>0.03 |

FIG. 5

BIOSENSOR FOR DETECTING THE PRESENCE OF CHOSEN ANALYTES

This is a continuation of application Ser. No. 08/124,914 filed Sep. 21, 1993 abandoned.

BACKGROUND OF THE INVENTION

A variety of disclosures exist which discuss the possibility of creating new biosensors that are both sensitive and selective and which are based on naturally occurring ion channel receptors, such as the nicotinic acetylcholine receptor. Included are the following representative disclosures: U.S. Statutory Invention Registration No. H201 to P. Yager; U.S. Pat. No. 5,001,048 to R. F. Taylor et al.; U.S. Pat. No. 5,111,221 to T. L. Fare et al.; M. Gotah et al., Analytical Letters, 20(6), 857–870 (1987); R. F. Taylor et al., Analytica Chimica Acta, 213 (1988) 131–138; M. E. Eldefrawi et al., Analytical Letters, 21(9), 1665–1680 (1988); L. B. Wingard, Jr. et al. and K. R. Rogers et al. in Biosensor Technology: Fundamentals and Applications (Marcel Dekker, N.Y., 1990), pp. 137–151 and 383–389, respectively; and M. Uto et al., Analytical Sciences, April 1990, Vol. 6, pp. 221–225. In the above disclosures, the ion channel receptor exists unconjugated to any other ligand having selective affinity for a desired analyte intended for detection. A recent general review of this area of technology is found in R. F. Taylor, "Immobilized Antibody—and Receptor-Based Biosensors", Bioprocess Technology 14, pp. 263–303 (1991).

A recent example of a biosensor including a lipid bilayer doped with ion channels is provided by U.S. Pat. No. 5,204,239. This reference shows the use of a supported, rather than suspended, lipid bilayer film containing an ion channel receptor to which a hapten can be joined to interact with a monoclonal antibody. The biosensor shown in this patent is a competitive immunoassay in which antibody attached to hapten conjugated to a receptor via cysteine residues prevents the formation of channels that are comprised of aggregates (e.g., 20–25) amino acid peptides. Introduction of excess hapten into solution produces a competition by the excess hapten for binding sites thus causing removal of antibody bound to the hapten on a channel forming protein allowing channel opening which can be measured by the appearance of an ion conduction channel. Such a biosensor has a number of potential disadvantages. In the type of competitive assay described, the amount of introduced hapten needs to be of the right concentration to remove bound antibody. If the concentration is too low the immunoassay may not function in an effective manner. The biosensor described in this patent is also not deemed to be effective with the use of large antibodies which, because they need to be on the receptor, might prevent a channel from forming in those instances when channel forming compositions are used.

SUMMARY OF THE INVENTION

The present invention relates to a novel immunoassay using a modified ion channel receptor as an essential component thereof for the detection of the presence of an unknown analyte in solution. The immunoassay of this invention comprises:

a) an ion channel receptor immobilized in a lipid film, which film is in contact with an ion-containing solution on each side thereof;

b) a ligand, conjugated to the receptor, said ligand having particular affinity for the analyte in solution, and, which, upon binding to the analyte in solution, causes an inhibition in ion flow through the channel; and c) means to detect the inhibition of ion flow through the channel in response to the binding of conjugated ligand and analyte.

In the immunoassay of the present invention, the ligand-ion channel receptor conjugation is a novel feature as compared to the previously described structures of the prior art.

DESCRIPTION OF THE DRAWINGS

The present invention is further illustrated by the Drawings, which form a part of the instant specification, wherein:

FIG. 5 gives the ELISA results confirming the formation of active bispecific antibody;

DESCRIPTION OF PREFERRED EMBODIMENTS

Figure 1:
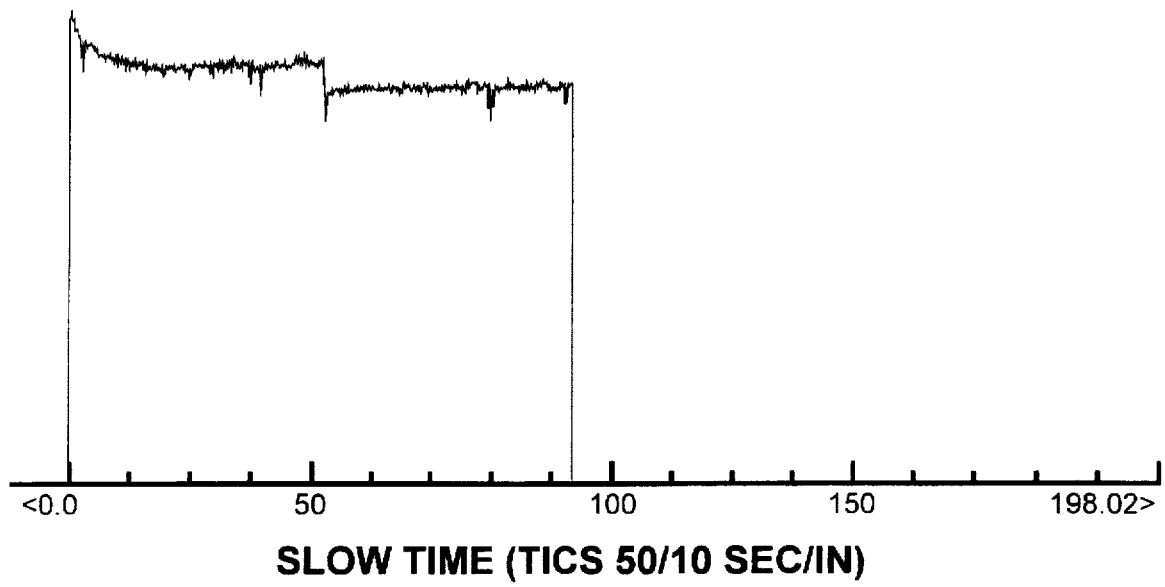
FIG. 1 illustrates a demonstration of the sensing principle of the instant invention by use of pseudo-bispecific antibodies.
Figure 1:
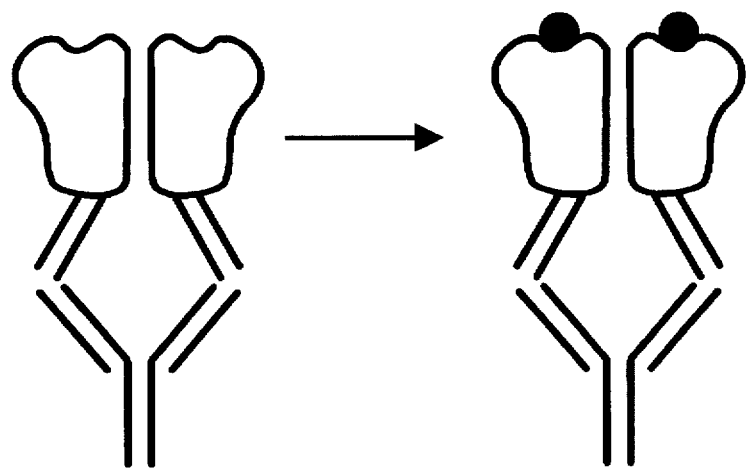

The isolation and purification of suitable ion channel receptors for use herein, such as those from the electric organ of the *Torpedo californica*, is well known to persons of ordinary skill in the art and is described, for example, by Lindstrom et al. in J. Biol. Chem., 255, 8340–8350 (1980), which is incorporated herein by reference, as well as other references. The crude membrane vesicles are preferably purified by alkaline extraction. A particularly preferred technique for isolation and purification of such receptors is described in Example 1, hereinafter. Other receptors of the same biological family as the nicotinic receptor (i.e. the glutamate and glycine receptors) can be expected to be suitable for modification as described herein. It may be useful to modify the ion channels derived from natural sources to eliminate the molecular processes of desensitization to agonist and channel inactivation, either of which would reduce detector sensitivity. This can be done by preparation of suitable derivatives of the natural protein or by assembling or synthesizing appropriate subsets of its amino acid sequence; such derivatives or facsimiles retain channel activity but lack agonist binding sites and inactivation gates. Potentially useful facsimiles of the nicotinic receptor channel protein reported in the existing literature include M2 delta and synporin.

The ion channel receptors can then be suitably reconstituted into either a planar bilayer lipid membrane or can be reconstituted into the bilayer lipid wall of liposomes (as shown in Example 2, hereinafter) in order to form a lipid film or structure which contain one or more ion channel receptors as an integral subcomponent. Such lipid film (or membrane)/ion channel receptor combinations form a necessary subcomponent in the lipid film (membrane)-ion channel receptor biosensors proposed by previous investigators.

The immunoassay of the present invention relies upon a lipid film-ion channel receptor subcombination which is a modified version of that previously proposed. The present invention relies, as an essential component, upon the additional presence of a "ligand" having particular affinity for the analyte to be detected by the immunoassay, which ligand is conjugated (or "bonded") to the ion channel receptor. When the thus modified receptor, immobilized in the lipid film, makes contact with the analyte, the bonding of ligand and analyte will change the configuration of the ion channel so that a difference in its functioning will occur, for example, its ability to allow for the flow of ions therethrough. This change in configuration of the ion channel receptor, upon bonding of analyte with the conjugated ligand moiety affords a basis for detection of the analyte.

In embodiments of the present invention, which are preferred embodiments herein, the ion channel receptor containing the conjugated ligand is immobilized in a film which is appropriately supported by a substrate of the type described and claimed in copending U.S. application Ser. No. 08/057,275, filed May 4, 1993, now abandoned and entitled "Biosensor Substrate for Mounting Bilayer Lipid Membrane Containing A Receptor". In such a mounted configuration the film containing receptor/ligand combination stretches across an open aperture in the floor of the biosensor substrate between two solutions on either side which allow for passage of charged ion molecules from one side of the film (or membrane) to the other through the receptor when in the open configuration in the absence of complementary "antiligand" in at least one of the solutions which will selectively bind to the "ligand" on the receptor. The presence of antiligand will close the receptor channels and will restrict ion flow through the ion channel receptor. Appropriate electronic means can detect the difference in the ion flow between the two conditions to provide a measure of antiligand in the system in the second described condition as compared to the first. Many electronic means are suitable for measurement of ion flow. These include current, voltage, capacitance and resistance measurements. In addition optical signals can be produced by incorporation of voltage sensitive and ion sensitive dyes. In instances where an excitatory light source is required to induce dye fluorescence this can also be provided. If the polyimide or similar structure is used as outlined in copending U.S. application Ser. No. 08/057,275, filed May 4, 1993, now abandoned one could introduce light through the transparent polyimide or similar structure itself.

The change in the conductance of the membrane as the ion channel opens or closes may be used at the signal from the detector. Alternatively, the detector may be embodied in a voltage-signalling configuration. In the latter configuration, standing ionic gradients to two ions are imposed in opposite directions across the membrane. The detector molecule would normally allow both to cross. A second ionophore, which allows passage of only one of the ions present is added. When both ionophores are open, the gradients of the two ions present can be set up so that the bi-ionic potential is near zero. When analyte is present, the detector molecule will be closed and only the second, more selective ionophore will allow current to flow. The potential will then go to the Nernst potential for the one ion that can cross the membrane.

The present invention can also be used in an assay in which the ligand-conjugated receptors are placed in the wall of a liposome rather than in a supported film as previously described. As indicated in Example 6, the reconstitution of solubilized ion channel receptor, voltage sensitive dye, and ligand but no antiligand, will provide only a higher level of fluorescence as compared to a system also containing the antiligand. The inhibition in the ability of carbamylcholine to open the ion channel receptor in the latter case can provide a means to measure the amount of antiligand.

The ligand to be selected for conjugation to the ion channel receptor can, for example, be Fab' fragments from the antibody to the analyte. This conjugation could be accomplished using disulfide bridges from the Fab' to the receptor. When the analyte is present, it will combine with two of the Fab' fragments and block the channel. To such a Fab' one can also conjugate, via disulfide bridge(s) or other means, a hapten to which antibodies or other compounds specifically bind. Alternatively, a bispecific antibody (of the general type described by Paulus in U.S. Pat. No. 4,444,878, which is incorporated herein by reference, and Science, Vol. 229, 1985, pp. 81–83) might be used. One arm of the bispecific antibody can be chosen to have affinity to the receptor while the other would be designed to have affinity with a chosen analyte to be detected in solution. The present invention, in its broadest context, contemplates the appropriate conjugation of a "ligand" to the ion channel receptor, the "ligand" being especially selected to bind to an "antiligand" which is the unknown analyte in solution and thereby cause a change in the ability of the ion channel receptor to allow the passage of ions therethrough. This change in the ability of the receptor to allow passage of ions therethrough can be appropriately measured to detect and quantitate the amount of unknown analyte. The biochemical ligand selected for use herein will normally be a protein and therefore have an amino function. Thus it may be an enzyme, antigen, antibody, receptor protein, other binding protein, or lectin, for example. However, it could also be a hapten, co-enzyme, electron mediator or other biologically reactive ligand, particularly one of low molecular weight. Thus, the biochemical ligand could be a sugar or steroid. It may have some other functional group than amino, for example a hydroxyl group or carboxyl group in steroid haptens. The basic concept of the ion channel receptor involves modification of the channel by attachment to the channel of a bispecific coupler that also recognizes analyte. Binding of the analyte to the coupler results in a change in the time-averaged channel conductance. This concept may be embodied in several different modes of interaction between the ion channel protein and the coupler. The mode of interaction could be direct, as in the Example in which the coupler, a bispecific antibody, binds to epitopes of the ion channel protein. In an alternative mode, the interaction could be by way of a prosthetic group conjugated to the coupler. In the latter configuration, the prosthetic group is chosen for its ability to interact with transmitter binding sites or allosteric modulatory sites on the ion channel, or to interfere with the conductive domains of the channel. Depending on the geometry of the complex of analyte and coupler, analyte binding would either favor, or sterically hinder, interaction of the ligand with its site of action on the ion channel. Examples of molecules potentially useful as prosthetic groups include competitive antagonists of acetylcholine such as a α-bungarotoxin, succinylcholine, and curare and its congeners. The present invention is further described by the Examples which follow.

EXAMPLE 1

This Example illustrates the isolation and purification of the nicotinic acetylcholine ion channel receptor (nAChR) which was used in later Examples.

Membrane vesicles enriched in nAChR from the electric organ of Torpedo californica were prepared according to the method described by Lindstrom et al., J. Biol. Chem. 255, 8340–8350 (1980). Subsequently, crude membrane vesicles were purified by alkaline extraction according to the method described by Montal et al., Ion Channel Reconstitution, p. 187 (1986) with the following modifications: The sucrose midbands enriched in nAChR were suspended in 60 ml of a solution which would become the solution inside the formed vesicles, the so-called "inside solution" (10 mM sodium phosphate buffer, pH 7.5, 10 mM $NaN_3$, and 400 mM TMACl), and were brought to a pH of 11.2 by adding 0.5 N NaOH. The alkaline membranes were centrifuged for sixty minutes at 30,000 rpm (105,000 g) in a Beckman 45 Ti rotor. The glassy pellets were brought back to a pH of 7.5 by suspension in 60 ml of "inside solution". The resulting suspension was recentrifuged at 105,000 g. The pH of the supernatant was checked, and if it was about 7.5, the pellets were prepared for further solubilization by suspending them in the "inside solution". Otherwise, if the pH was above 7.5, the pellets were resuspended in the "inside solution" to 60 ml, and the washing step was repeated.

EXAMPLE 2

This Example illustrates the solubilization and constitution of nAChR from Example 1 into liposomes.

Solubilization of nAChR was performed according to the procedures used by Anholt et al., J. Biol. Chem. 257(12), 7122–7134 (1981). The nAChRs purified by alkaline extraction were solubilized in 2% sodium cholate (Sigma Chemical Co., St. Louis, Mo.) which had been recrystallized according to the method of Kagawa and Racker, J. Biol. Chem., 246(17), 5477–5487 (1971), 5 mg/ml (stock of 100 mg/ml) phosphatidylcholine type IIS (Sigma Chemical Co., St. Louis, Mo.) and "inside solution". The final solubilized mixture had a ratio of sodium cholate:lipid:protein of 8:2:1. Unsolubilized membranes were removed by centrifugation at 124,000 g for 30 min in a Beckman type 40 rotor (Beckman, Redmond, Wash.) at 37,000 rpm. "Inside solution" was added to dilute the cholate concentration to 1.2%. The protein concentration was determined by the method of Bradford in Anal. Biochem., 72, 248–254 (1976).

The lipids to be used in reconstitution were prepared as follows: First, 100 mg/ml lipid (80% L/α-phosphatidylcholine and 20% cholesterol) was made up in 25 ml of distilled water. The lipids were dispersed in water by an indirect sonication technique in which the flask containing the lipid solution was placed in a sonicated water bath for one half hour. A sonicator cell disrupter, Model W 185 F (Heat Systems-Ultrasonic, Inc., Plainview, N.Y.) was used at a micro tip setting of 5. Nitrogen gas was bubbled into the dispersed lipids through a small hose. Yellow homogenized lipids were usually obtained after forty minutes of indirect sonication.

The reconstitution was performed using methods similar to Wan and Lindstrom, Biochemistry, 24, 1212–1221 (1985). Reconstitution of solubilized nAChR into liposomes was obtained after forty-eight hours of dialysis against a 250 volume of flux buffer (10 mM sodium phosphate buffer pH 7.5, 10 mM $NAN_3$, 400 mM TMACl) in a Spectra/Por molecular porous membrane tubing, (VWR Scientific, Los Angeles, Calif.). When protein elements (Mab, Fab', Bab, and/or analyte) were to be incorporated into the "inside solution", they were added before the dialysis. An ultrafiltration technique utilizing a CENTRICON-100 ultrafiltration apparatus (Amicon, Beverly, Mass.) was used to quantify the receptors. The ultrafiltration method involved the use of 100 kD molecular weight cutoff membranes to allow for separation of unbound 8 kD α-bungarotoxin labeled with fluorescein-isothiocyanate (FITC), from that which is bound to the 258 kD nAChR-toxin complex.

EXAMPLE 3

This Example illustrates the preparation of monoclonal antibodies for use in later Examples.

A mAb 148 rat hybridoma was obtained from Dr. J. M. Lindstrom of the University of Pennsylvania. This cell line was then cloned to isolate high producing colonies. Large quantities of mAb 148 were produced in the peritoneal cavity of irradiated mice. A antibody, BIg 73, was used as a control while the antibody, BIg 715, was used as a control and was digested to Fab' fragments, then conjugated to Fab' fragments of mAb 148 to form the bispecific Ab. BIg 715 is specific for bovine IgG, while BIg 73 is specific for bovine IgM. Both BIg 73 and BIg 715 are mouse monoclonal $IgG_1$ antibodies and were made available by Dr. W. C. Davis of Washington State University. Bovine IgM used to verify bispecific antibody activity in ELISAs and as a model analyte, was obtained from Sigma Chemical Co., (St. Louis, Mo.).

Rat $IgG_{2B}$ (mAb 148) anti-nAChR antibody, and mouse $IgG_1$ anti bovine IgG and anti bovine IgM were affinity purified on agarose coated with antirat-IgG and anti-mouse-IgG columns (Sigma Chemical Co., St. Louis, Mo.), respectively. Column elution was accomplished using 0.1 M glycine/HCl buffer having a pH of 2.4 to 2.6. IgG purity was verified using Laemmli's procedure as described in Nature, Vol. 227, p. 680 (1970) in SDS-PAGE gels of 10–12% acrylamide concentration. Finally, rat and mouse radial immunodiffusion plates, $IgG_{2a}$ and $IgG_1$, respectively, (The Binding Sites, Gaithersburg, Md.), were used for mAb quantitation.

EXAMPLE 4

This Example describes the action of carbamylcholine on ion channel receptors immobilized in liposomal walls as monitored by measurement of a voltage sensitive fluorescent dye.

The function of reconstituted nAChRs was tested by placing the vesicles containing the nAChR in a solution of ionic concentration different from that of the interior liquid and monitoring voltage changes on introduction of carbamylcholine (Sigma Chemical Co., St. Louis, Mo.). The slow response voltage sensitive fluorescent dye bis-(1,3-dibutylbarbituric acid)trimethine oxonol [$DiBAC_4(3)$J], (Molecular Probes, Eugene, Oreg.), was used for this purpose and fluorescence was monitored with a SLM 500 Spectrofluorometer (SLM Instruments, Urbana, Ill.). To a cuvette containing a 0.6 mm magnetic stirring bar, 2 ml of outside solution (10 mM sodium phosphate buffer, pH 7.5, 10 mM $NaN_3$, 400 mM KCl) was added and was followed by the addition of 50 µl of liposome preparation and 2 µl of a 37.5 µM dye. The liposome preparation had been preloaded with dye so that the approximate internal concentration of dye was 3.75 nM. The liposome mixtures used in the various experiments contained differing amounts of nAChR. In each case, protein content was determined by the modified Lowry method (M. A. K. Markwell et al., Anal. Biochem. (1978) 87:206–210). For the agonist studies, nAChR levels were determined to be on the order of 25 µg/ml. Unilammellar liposomes were obtained by a one minute sonication and followed by a one half hour incubation at 4° C. Fluorescence was observed in the spectrofluorometer for about thirty seconds or until it reached a steady level. Ten µl of carbamylcholine with a final concentration of 13.4 μM was injected through a 40 μl Hamilton syringe to the cuvette inducing the opening of nAChR channels and an influx of K⁺ ions. This influx resulted in positive/polarization of the membrane liposomes and subsequent fluorescence enhancement.

EXAMPLE 5

This Example illustrates the manner in which the carbamylcholine-induced ion channel receptor activity measurements described in Example 4 can be affected by the state of the nAChR that is incorporated in the vesicles.

Solubilization of the nAChR was performed as described in Example 2. Reconstitution of the nAChR into vesicles was then performed using the following three conditions:

1. Only the solubilized nAChR was used. This was a duplication of the method employed in Example 2.
2. Solubilized nAChR plus the Ab fragment of the monoclonal antibody to the receptor, mAb-148, was also included during reconstitution at an approximate equivalent ratio of 10:1 (Fab' fragment:nAChR). It was assumed that substantially all of the receptors had Fab' fragment attached thereto.
3. Solubilized nAChR, Fab' fragment and an antibody to F(ab')$_2$ were included during reconstitution at an approximate equivalent ratio of anti-F(ab')$_2$ to Fab' of 3:1. It was assumed that substantially all of the receptors would be in the nAChR-Fab'-anti-F(ab')$_2$ state.

The activity of the functional assay conducted using the second reconstitution protocol, described above, was only slightly reduced as compared to that of Example 5 which used the first reconstitution protocol (a duplication of Example 2).

Carbamylcholine was unable, however, to open the receptor channels when the third protocol was employed indicating that nAChRs tagged with Fab' fragments were blocked by introduction of the anti-F(ab')$_2$ antibodies.

EXAMPLE 6

This Example provides quantitative comparisons of fluorescence changes observed in experiments like those outlined in Example 5.

The concept of blockade by cross-linking by monitoring the effect of anti-rat-F(ab')$_2$ on receptors that had been coupled to the Fab' from mAb 148 was tested herein. MAb 148, in itself, blocks conduction through the nAChR. Receptors were solubilized and then incorporated into vesicles either normally, or after incubation with Fab' or after incubation with Fab' and anti-F(ab')$_2$. The experiment was really in two parts. Initially, the functional assay was performed with 100 μl of vesicles. This was later determined to be too high, and the inoculation was subsequently reduced to 50 μl. The first comparison was between vesicles containing only native nAChR and vesicles containing Fab' coupled to nAChR. The second comparison was between the effect of 100 and 50 μl of inoculation of vesicles containing Fab'-coupled receptors. The third comparison was between 50 μl inoculations of Fab'-coupled receptors and anti-F(ab')$_2$-Fab' coupled receptors.

TABLE 1

| | Condition | Vol (μl) | ΔF/F |
|---|---|---|---|
| First | control | 100 | .22 |
| Comparison | Fab' | 100 | .18 |
| Second | Fab' | 100 | .18 |
| Comparison | Fab' | 50 | .10 |
| Third | Fab' | 50 | .10 |
| Comparison | anti-F(ab')$_2$ | 50 | −.04 |

The effect of coupling Fab' onto the receptor was not significant and as expected, half the number of vesicles gave approximately half the change in fluorescence. Finally, activity was completely lost in the anti-F(ab')$_2$-Fab' coupled receptors.

Figure 2:
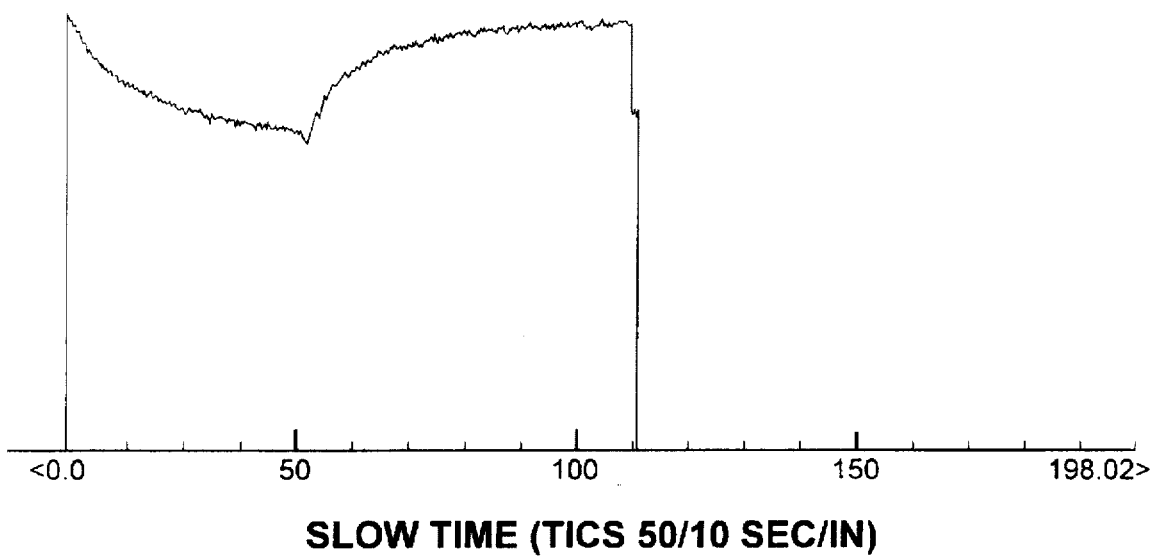
FIG. 2 illustrates the results obtained using control vesicles receiving only Fab' anti-nAChR fragments.
Figure 2:
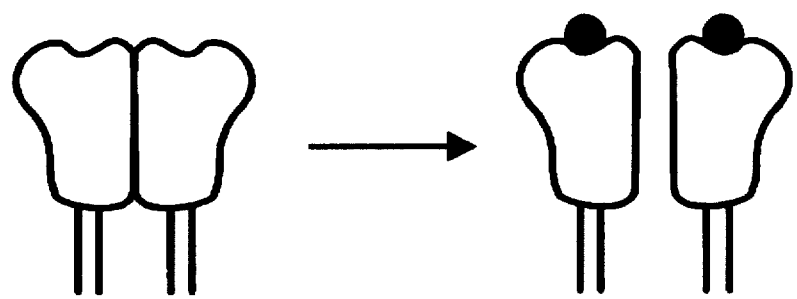
Figure 3:
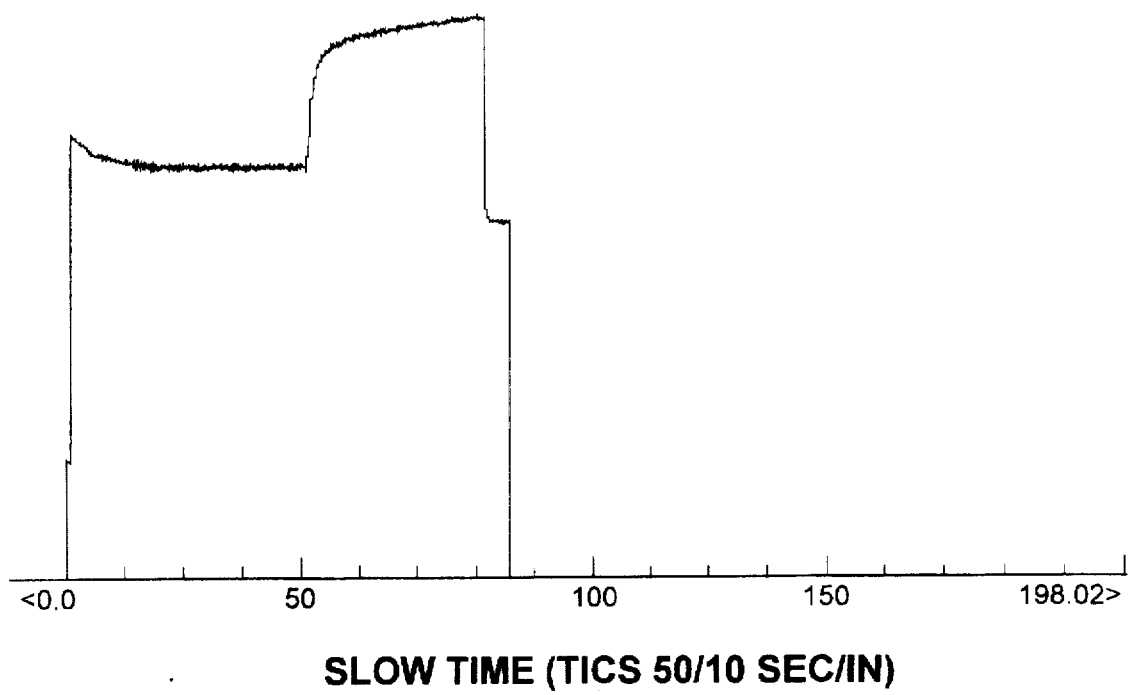
FIG. 3 illustrates the results obtained using control vesicles receiving only the nAChR antagonist carbachol.
Figure 3:
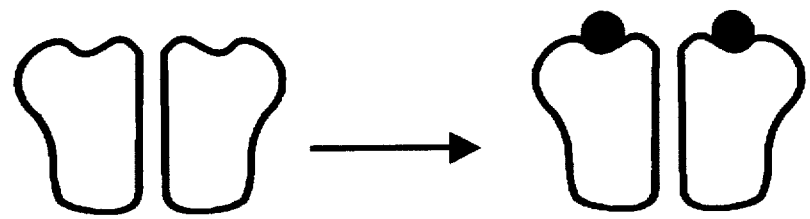

The above experiments are shown diagrammatically in FIGS. 1–3. FIG. 1 shows the instance in which the receptor's two binding sites for Fab' were cross-linked by the anti-Fab'. In this case, the combination of the two Fab's and the anti-Fab' simulates the complex of two bispecific Abs plus analyte. This experiment showed that Ab-analyte complexes of at least the dimensions of 2 Fab'+1 Ab could block the channel. Also, it suggested that channel blockage was not especially sensitive to the molecular geometry of the cross-linker between the two Fab' binding sites. This would be important for application of this mechanism to detection of a wide range of analytes. Control vesicles received either Fab' alone (FIG. 2) or neither Fab' nor anti-Fab' (FIG. 3). Both controls showed the normal pattern of large increases in fluorescence on addition of carbamylcholine agonist. Hence, addition of Fab' does not block the channel while cross-linking by simultaneous attachment to two Fab3 s on the same nAChR does cause blockade as shown in FIG. 1.

EXAMPLE 7

This Example illustrates how the nicotinic acetylcholine receptor discussed in Examples 1–6 can be modified by attachment of a bifunctional ligand that both recognizes the receptor and an analyte of interest.

Figure 4:
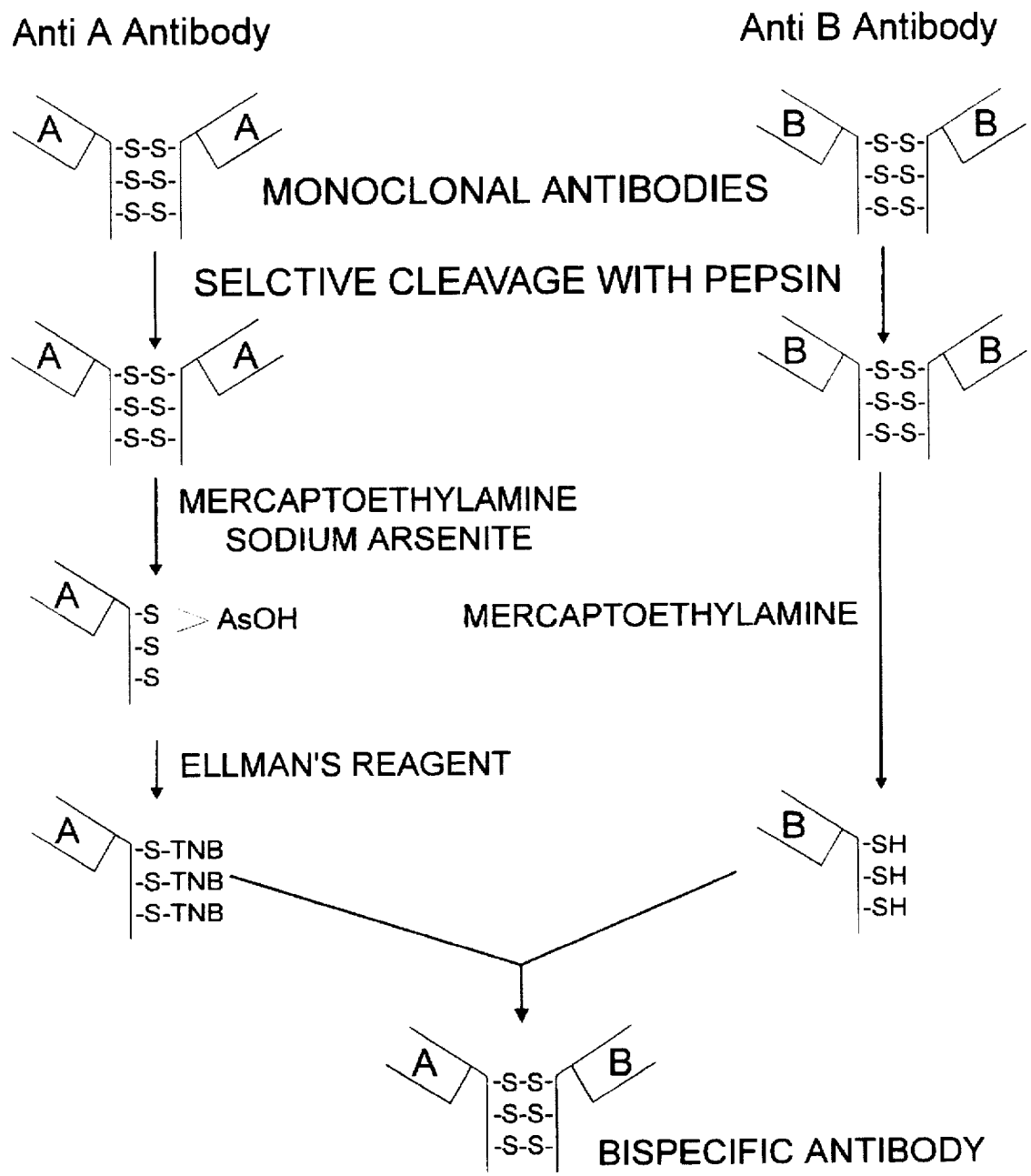
FIG. 4 illustrates a schematic representation of the procedure used to produce bispecific antibody.

Bispecific antibodies are examples of ligands that recognize two different molecules. For example, one Fab' half of a bAb may bind to an acetylcholine receptor which the other half recognizes an analyte (see FIG. 4). Purified antibody was digested with pepsin to yield F(ab')$_2$. The resulting F(ab')$_2$ was reduced by addition of 2-mercaptoethylamine. Solid 5,5'-dithio-bis(2-nitrobenzoic acid) was then added to form a thio-nitrobenzoic acid derivative of each of the Fab3 s (Fab'-TNB). The free form of the Fab' fragment of one of the antibodies was regenerated from Fab'-TNB by reduction. The free Fab' of one antibody was then incubated overnight with an approximately equimolar amount of the Fab'-TNB of the second antibody. The bAb so produced was then purified and ready for use.

The test activity of the bispecific Ab and ELISA technique was employed. First, a 96-well plate was coated with poly-L-lysine overnight, washed with buffer, followed by overnight addition of nicotinic acetylcholine receptor (nAChR) and another wash step. Next, the primary antibodies, either mAb 148, BIg 715, or bAb were added to the wells and allowed to incubate for two hours at room temperature. The wells were washed with washing buffer to remove any unbound antibody. A peroxidase-labelled secondary antibody was then added to the wells and the mixtures were incubated for one hour at room temperature. Again, unbound antibody was removed by washing the wells with washing buffer. A peroxidase substrate coloring reagent was then added to each of the wells. After 20 minutes, the absorbance at 405 nm was measured with a plate reader. Only wells in which the primary antibody binds to the nAChR and the secondary antibody recognizes the primary antibody developed significant color. To fully test the BIg 715 activity of the bispecific antibody (bAb), bovine IgG (to which BIg 715 binds) was added to some wells in which bAb was the primary antibody. Bovine IgG served as an antigen in this case. The secondary antibody was an anti-bovine IgG. The important results including those from appropriate controls are summarized below.

From column 1 of FIG. 5, one sees from the color change that the nAChR-bound rat mAb 148 was indeed recognized by the anti-rat-Fab' peroxidase-labeled antibody. As expected, neither the anti-mouse nor the anti-bovine IgG secondary antibodies cross reacted with mAb 148. When bAb was added to nAChR-containing wells, the bAb half that recognized the nAChR bound. The colorimetric change induced by both the peroxidase-labeled anti-rat and anti-mouse confirmed the presence of both halves of the bAb. The anti-bovine-IgG Ab did not cross react with the mouse half of the bAb. The analyte specific end of the nAChR-bound bAb recognized and bound to the bovine IgG as indicated by the positive peroxidase reaction when adding labeled anti-bovine-IgG Ab. Controls showed that the BIg 715 dimer did not show specificity for the nAChR or anything on the plate, and that bovine IgG did not recognize mAb 148, nAChR nor any other component on the plate.

EXAMPLE 8

This Example illustrates how the carbamylcholine-induced ion channel receptor activity described in Example 4 can be made specific for a given analyte by using a bifunctional ligand.

The hybrid antibody specific to the nAChR on one end and to bovine IgG on the other was tested as a prototype of the sensor. There was a strong suggestion in these experiments that cross-linking the receptor had an effect on incorporation of the receptor complex into vesicles. The change in fluorescence that occurred after carbachol administration showed two time constants. The rapid change presumably reflected the change in voltage across unilammellar vesicles and was the change that was desired for monitoring. The slower change reflected other processes including possibly, diffusion of either dye or carbachol into polylammellar lipids.

Prior to using the bispecific antibody preparation, the kinetics of fluorescence change were quite uniform; about 65% of the total fluorescence change was rapid. As Table 2 shows, the fraction of the total response that was rapid changed when the antibodies were cross-linked with analyte. In addition, the carbachol induced increase in fluorescence also changed, in accordance with the original idea.

TABLE 2

| Condition | Fast ΔF/Σ ΔF | Fast ΔF/F$_0$ |
| --- | --- | --- |
| Control | 0.64 | 0.118 |
| + bAb | 0.67 | 0.155 |
| + bAb + BIg 715 | 0.47 | 0.116 |
| + bAb + bovine IgG | 0.01 | 0.004 |
| + bAb + anti-mouse | 0.05 | 0.019 |

Coupling of the bispecific antibody to the nAChR did not change the fraction of the total fluorescence change that occurred rapidly and, in this experiment, increased the rapid ΔF/F$_0$. This latter change was probably not significant. When the coupled receptor was incubated with a control protein (BIg 715), prior to incorporation, there was a slight decrease in the fraction of the total ΔF that occurred rapidly, but no decrease in desired signal (fast ΔF/F$_0$). However, incubation of the coupled receptor with analyte (bovine IgG) blocked the initial ΔF almost completely. It also strikingly reduced the fraction of the total fluorescence.

The anti-mouse Ab consists of polyclonal antibodies that recognize the analyte specific Fab' fragment of the bispecific Ab, but do not recognize the analyte binding region itself. The action is the same as that of the analyte, conductance is blocked and there is a reduction in the fraction of the ΔF that occurs rapidly. Since the polyclonals recognize a variety of protein sequences on the analyte-specific-Fab' they demonstrate that it is the modification of the protein sequence on the ligand that is attached to the nAChR that is important in varying specificity of a resulting sensor. The specific recognition of bovine IgG on the other hand demonstrates a way in which sensors can be tailor made for any desired analyte.

EXAMPLE 9

This Example illustrates how carbamylcholine-induced ion channel receptors reconstituted in bilayer lipid membranes were inactivated when analyte, bovine IgG, came in contact with bispecific antibodies attached to the nicotinic acetylcholine receptors (nAChRs).

Solubilization and Constitution of nAChRs into Liposomes

Solubilization of nAChR was performed according to the procedures used by Anholt et al., supra. The nAChRs, purified by alkaline extraction, were solubilized in 2% sodium cholate (Sigma), which had been recrystallized according to the method of Kagawa & Racker, supra, 5 mg/ml (stock of 100 mg/ml) of L/α-phosphatidylcholine type IIS (Sigma) and "inside solution". The final solubilized mixture had a ratio of sodium cholate:lipid:protein of 8:2:1. Unsolubilized membranes were removed by centrifugation at 124,000 g for thirty minutes in a Beckman type 40 rotor at 37,000 rpm. "Inside solution" was added to dilute the cholate concentration to 1.2%. The protein concentration was determined by the method of Bradford, supra.

Reconstitution was performed using methods similar to Wan & Lindstrom, supra. Reconstitution lipid was added to the solubilized receptor so that the concentrations of protein:lipid:cholate were 0.2, 5 and 1.2% respectively. This mixture was dialyzed against 250 volumes of inside solution with one solution change over in a forty-eight hour period. As the cholate was dialyzed away, multilamellar liposomes were formed which included nAChR. From this preparation, unilamellar liposomes were prepared by indirect sonication just prior to experimentation.

Protein determinations on the reconstituted liposome preparations were made using an amido-black reaction (Schweikl et al., J. Biol. Chem., 264, 11136–11142, 1989). Receptor quantity was determined from the binding of FITC-labeled α-bungarotoxin. The bound toxin was separated from the unbound by the use of Centricon-100 ultrafilters, and 1 mM nicotine was used to block the receptors in order to determine non-specific binding. Generally, about 3% of the total protein was nAChR. Total protein concentration in the reconstituted vesicles ranged between 2 and 6 mg/ml. The concentration of nAChR was thus between 3.1 and 9 μg/ml (12–36 nM) in the different preparations.

Formation of Lipid Bilayer Membranes including nAChR

Lipid bilayers were formed on a Kel-F chamber in a PVC holder from Warner Instrument Corp. (Hamden, Conn.). The chamber was conditioned by the addition of a drop of 5% soybean lipid in n-decane over the pore area. This was allowed to dry. The chamber was then put into its holder and both outside (cis side) and inside (trans) were filled with flux solution (400 mM KCl+10 mM sodium phosphate buffer at pH 7.5). Reconstituted receptors were added to a 5% soybean lipid in n-decane in a ratio of 1 to 100. This mixture was indirectly sonicated for ten minutes. A temporary emulsion was made by up-down pipetting, and this emulsion was painted over the pore using a glass stir bar. A bilayer was formed that contained the receptors.

Electrical Recording

Data acquisition and analysis was done using the Axon Fetchex acquisition and Fetchan analysis programs. Holding potential was normally between 100 and 165 mV cis side positive. Holding potentials that were lower or of opposite polarity also showed activity. The raw data were current readings as a result of channel openings.

Blocking Channel Activity nAChRs incorporated into BLMs were activated by the addition of carbamylcholine. Various experiments were conducted in order to test the ability of mAb 148 and bispecific antibody (BsAb) to block channel activity. In the first set of experiments, a 5 nM concentration of mAb was added to active membranes. In other experiments, BsAb alone and BsAb followed by bovine IgG were added to the trans side of a BLM with active channels. Channel activity was monitored after the addition of these Abs and to the membrane.

Character of nAChR Activity

Figure 6:
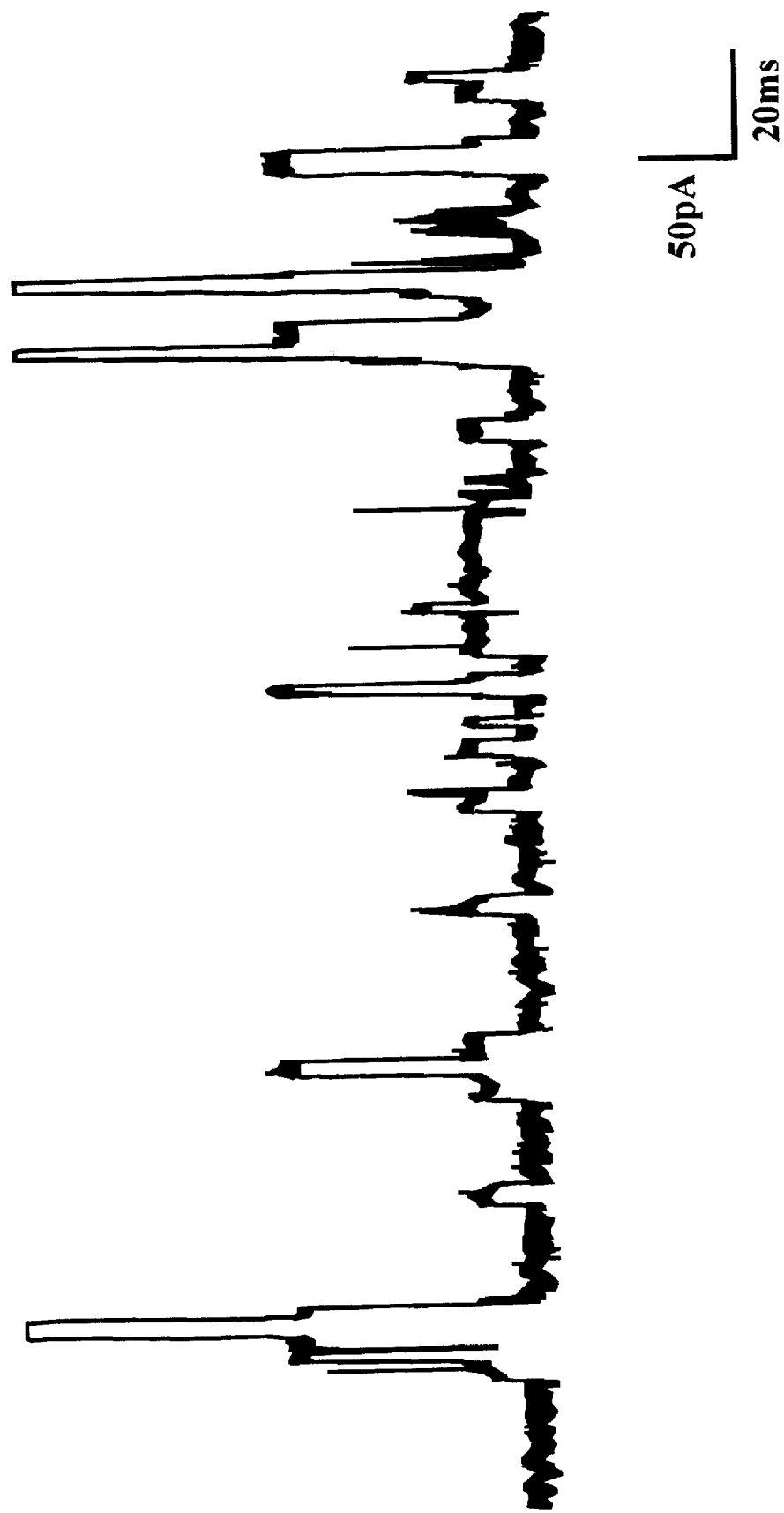
FIG. 6 shows a typical current trace from recording of active nAChR reconstituted in bilayer lipid membranes with single channel (smaller steps) and multichannel (larger steps) opening events in the trace (average open time duration of 3.1±0.45 ms)

There is little activity before the agonist carbamylcholine (CCh) was added, and CCh at concentrations between 0.2 and $2 \times 10^{-5}$ were added to the cis side of the chamber. The channel then showed bursts of openings typical of the nAChR. The concentration of CCh used was less than that required for maximum activity, but was one that produced only a moderate amount of desensitization (Anholt et al., The *Enzymes of Biological Membranes*, pp. 335–401, 1984). A typical set of experimental traces is shown in FIG. 6. Here, average open duration of single channels is 3.1±0.45 ms. The open duration of non-desensitized nAChR with CCh averaged 3.9±0.41 ms in the work of Hess et al., Am. Rev. Biophys. Bioeng., 12, 442–473 (1983). Average open duration is much shorter in the fully desensitized receptor.

In the native state, receptors are tied together by a linker protein (Chang & Block, Biochemistry, 16, 4513–4520, 1977). The purification procedures used here do not fully dissociate the receptor and most of receptors appear as dimers. In the preparation, the apparent single channel events were actually the ganged opening of a pair of channels. The larger channel events were predominantly the ganged opening of a 9 channel unit. We would estimate there were between 4 and 6 ganged double units present, as well as the 9 channel unit.

Addition of a Known Channel Blocking Ab

The antibody mAb 148 is known to block nAChR when it is in divalent form (Blatt et al., J. Neurosci., 6, 481–486, 1986). When added to the trans chamber at a final concentration of 5 nM, all channels were blocked within thirty seconds. The experiment corroborates the work of Blatt et al. as well as serving as a control for the subsequent BsAb/analyte experiments.

Addition of Bispecific Ab

Figure 7:
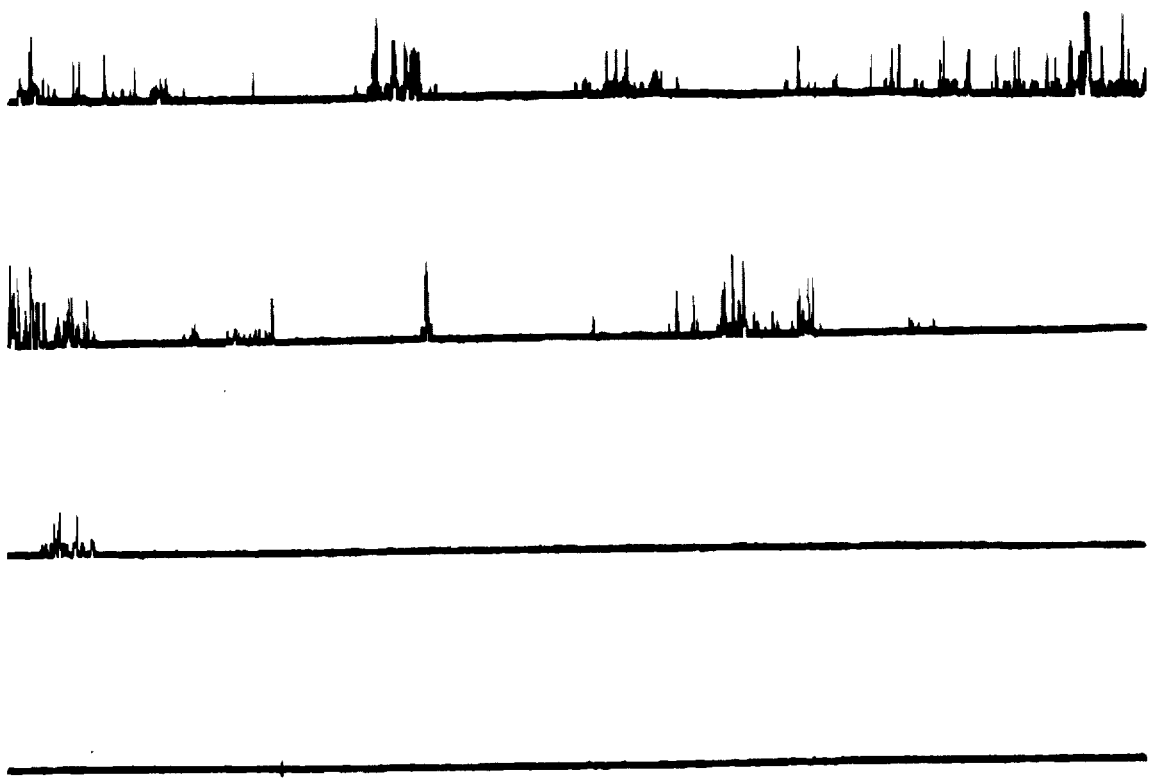
FIG. 7 illustrates current traces showing disappearance of nAChR current activity on exposure to bovine IgG analyte.

BsAb was added on the cis side so that the final concentration was 3 nM. No changes in the kinetic parameters of the channel or in the degree of ganging were observed over a period of ten minutes. At that time, the analyte, bovine IgG, was added to the cis side so that its final concentration was 37 nM. FIG. 7 is a continuous trace of the time between sixteen and thirty-two seconds after addition of analyte. Immediately after addition, there was a transient increase in apparent ganging although there was little or no change in the rate constants of the receptor. That is burst and interburst duration, as well as open and closed duration during a burst were little changed. However, within thirty seconds of addition, all channel activity was permanently blocked.

Concentration Dependency

The response of mAb 148 at 5 nM and of bovine IgG at 37 nM was encouraging. First, these concentrations were already quite low, and the response time of ten seconds was excellent. Second, in these experiments the chambers were not vigorously stirred; rather, Abs were added by a pipette, and the pipette plunger is pushed up and down a few times. In other work (U.S. application Ser. No. 08/057,275, filed May 4, 1993 now abandoned) it as shown that the membranes maintained their integrity for up to fifty hours even in the presence of constant mixing with a magnetic stir bar. This is important because with better stirring it would not be expected that mass transfer limitations would impede sensing capabilities even at concentrations of 100 times less than what were studied or even lower concentrations. Hence, as long as dissociation constants were not a limitation, it would be expected that sensing concentration limits would reach far below the nM level.

The foregoing Examples are presented for illustrative purposes only and should not be construed in a limiting sense. The scope of protection sought is set forth in the claims which follow.

We claim:

1. A biosensor for use in a non-competitive immunoassay for detecting the presence of a chosen analyte in solution which comprises:
   a) an ion channel receptor immobilized in a suspended lipid film which film is in contact with an ion-containing solution on each side thereof;
   b) a ligand, conjugated to the receptor, said ligand which specifically binds to the analyte in solution, and, which, upon binding to the analyte in solution, causes an inhibition in ion flow through the ion channel; and
   c) means to detect the inhibition of ion flow through the ion channel in response to the binding of conjugated ligand and analyte.

2. A biosensor as claimed in claim 1 wherein the receptor is the nicotinic acetylcholine receptor.

3. A biosensor as claimed in claim 1 wherein the lipid film is in the form of a membrane.

4. A biosensor as claimed in claim 2 wherein the lipid film is in the form of a membrane.

5. The biosensor as claimed in claim 1 wherein the ligand which is conjugated to the receptor is a bispecific antibody which has one arm which specifically binds the receptor and another arm which specifically bids the chosen analyte to be detected in solution.

6. The biosensor as claimed in claim 2 wherein the ligand which is conjugated to the receptor is a bispecific antibody which has one arm which specifically binds the receptor and another arm which specifically binds the chosen analyte to be detected in solution.

7. The biosensor as claimed in claim 3 wherein the ligand which is conjugated to the receptor is a bispecific antibody which has one arm which specifically binds the receptor and another arm which specifically binds the chosen analyte to be detected in solution.

8. The biosensor as claimed in claim 4 wherein the ligand which is conjugated to the receptor is a bispecific antibody which has one arm which specifically binds the receptor and another arm which specifically binds the chosen analyte to be detected in solution.

9. The biosensor as claimed in claim 1 wherein the ligand which is conjugated to the receptor is a Fab' fragment which specifically binds with the chosen analyte to be detected in solution.

10. The biosensor as claimed in claim 2 wherein the ligand which is conjugated to the receptor is a Fab' fragment which specifically binds with the chosen analyte to be detected in solution.

11. The biosensor as claimed in claim 3 wherein the ligand which is conjugated to the receptor is a Fab' fragment which specifically binds with the chosen analyte to be detected in solution.

12. The biosensor as claimed in claim 4 wherein the ligand which is conjugated to the receptor is a Fab' fragment which specifically binds with the chosen analyte to be detected in solution.

13. A biosensor as claimed in claim 1 wherein the detection means (c) are electronic.

14. A biosensor as claimed in claim 1 wherein the detection means (c) are optical.

15. The biosensor as claimed in claim 1 wherein the ligand, which is conjugated to the receptor, is a Fab' fragment and the Fab' fragment is also linked to a hapten to which the chosen analyte to be detected in solution will bind.

16. The biosensor as claimed in claim 2 wherein the ligand, which is conjugated to the receptor, is a Fab' fragment and the Fab' fragment is also linked to a hapten to which the chosen analyte to be detected in solution will bind.

17. The biosensor as claimed in claim 3 wherein the ligand, which is conjugated to the receptor, is a Fab' fragment and the Fab' fragment is also linked to a hapten to which the chosen analyte to be detected in solution will bind.

18. The biosensor as claimed in claim 4 wherein the ligand, which is conjugated to the receptor, is a Fab' fragment and the Fab' fragment is also linked to a hapten to which the chosen analyte to be detected in solution will bind.

* * * * *

UNITED STATES PATENT AND TRADEMARK OFFICE
CERTIFICATE OF CORRECTION

PATENT NO.    : 5,736,342
DATED         : April 7, 1998
INVENTOR(S)   : Van Wie et al.

It is certified that error appears in the above-identified patent and that said Letters Patent is hereby corrected as shown below:

Column 1,
Before Line 6, should include the following:

-- ACKNOWLEDGMENT OF GOVERNMENT SUPPORT

This invention was made with government support under National Science Foundation grant no. ECE-8609910. The U.S. government has certain rights in this invention. --

Signed and Sealed this

Ninth Day of July, 2002

*Attest:*

*Attesting Officer*

JAMES E. ROGAN
*Director of the United States Patent and Trademark Office*